US010279060B2

(12) United States Patent
Deprey et al.

(10) Patent No.: US 10,279,060 B2
(45) Date of Patent: May 7, 2019

(54) SYSTEM FOR DECONTAMINATION OF A LUMEN DEVICE

(71) Applicant: Medivators Inc., Minneapolis, MN (US)

(72) Inventors: Eric J. Deprey, Prior Lake, MN (US); Michael P. Petersen, Eden Prarie, MN (US); Robert F. Mosher, Spring Park, MN (US)

(73) Assignee: Medivators Inc., Minneapolis, MN (US)

( * ) Notice: Subject to any disclaimer, the term of this patent is extended or adjusted under 35 U.S.C. 154(b) by 393 days.

(21) Appl. No.: 15/138,379

(22) Filed: Apr. 26, 2016

(65) Prior Publication Data

US 2016/0317688 A1 Nov. 3, 2016

Related U.S. Application Data

(60) Provisional application No. 62/153,943, filed on Apr. 28, 2015.

(51) Int. Cl.
*A61L 2/20* (2006.01)

(52) U.S. Cl.
CPC .......... *A61L 2/208* (2013.01); *A61L 2/20* (2013.01); *A61L 2202/122* (2013.01); *A61L 2202/24* (2013.01)

(58) Field of Classification Search
CPC .................................. A61L 2/208; A61L 2/20
See application file for complete search history.

(56) References Cited

U.S. PATENT DOCUMENTS

| 5,785,934 | A | * | 7/1998 | Jacobs | ...................... A61L 2/14 422/1 |
|---|---|---|---|---|---|
| 6,423,266 | B1 | | 7/2002 | Choperena et al. | |
| 2001/0036422 | A1 | | 11/2001 | Lin et al. | |
| 2004/0091389 | A1 | | 5/2004 | Malkin et al. | |
| 2005/0147527 | A1 | | 7/2005 | Brown et al. | |
| 2005/0260097 | A1 | | 11/2005 | Williams et al. | |
| 2007/0100206 | A1 | * | 5/2007 | Lin | ......................... A61B 1/123 600/156 |

(Continued)

FOREIGN PATENT DOCUMENTS

EP 1016421 A1 7/2000

OTHER PUBLICATIONS

International Search Report and Written Opinion issued in PCT/US2016/029771, dated Apr. 28, 2016, 11 pages.

(Continued)

*Primary Examiner* — Donald R Spamer
(74) *Attorney, Agent, or Firm* — Faegre Baker Daniels LLP

(57) ABSTRACT

A system for decontamination of a medical device comprising a decontamination chamber configured to withstand pressure changes; a vacuum pump configured to adjust the pressure within the decontamination chamber; and a source of decontaminating substance positioned within the decontamination chamber. The system also includes a container within the decontamination chamber to enclose a medical device and provide fluid communication between the medical device and the source of decontaminating substance; and a vaporizer positioned within the decontamination chamber to vaporize the decontaminating substance.

20 Claims, 6 Drawing Sheets

(56) References Cited

U.S. PATENT DOCUMENTS

| | | | |
|---|---|---|---|
| 2010/0272603 A1* | 10/2010 | Goncalves | A61L 2/208 422/37 |
| 2011/0092766 A1* | 4/2011 | Monassevitch | A61B 1/0008 600/104 |
| 2011/0135537 A1 | 6/2011 | Schwartz et al. | |
| 2015/0202339 A1 | 7/2015 | Schwartz et al. | |
| 2015/0336139 A1 | 11/2015 | Deprey et al. | |

OTHER PUBLICATIONS

International Search Report and Written Opinion issued in PCT/US2018/020198, dated Jun. 27, 2018.
International Preliminary Report on Patentability issued in PCT/US2016/029771, dated Nov. 9, 2017, 7 pages.

* cited by examiner

SYSTEM FOR DECONTAMINATION OF A LUMEN DEVICE

CROSS-REFERENCE TO RELATED APPLICATION(S)

This application claims the benefit of priority to U.S. Provisional Application No. 62/153,943, filed Apr. 28, 2015, which is herein incorporated by reference in its entirety.

TECHNICAL FIELD

The present disclosure relates to decontamination of devices, such as medical devices. More particularly, the present disclosure relates to systems, containers and methods for decontaminating lumen medical devices.

BACKGROUND

Robust medical equipment is often sterilized at high temperatures. Commonly, the equipment is sterilized in a steam autoclave under a combination of high temperature and pressure. While such sterilization methods are effective for more durable medical instruments, advanced medical instruments formed of rubber and plastic components with adhesives are delicate and often unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Further, endoscopes can also present problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

SUMMARY

Disclosed herein is a system for decontamination of a medical device comprising a decontamination chamber configured to withstand pressure changes; a vacuum pump configured to adjust the pressure within the decontamination chamber; and a source of decontaminating substance containing hydrogen peroxide or peracetic acid and positioned within the decontamination chamber. The system also includes a container configured to be received within the decontamination chamber, the container forming an enclosed space and configured to enclose a medical device and provide fluid communication between the medical device and the source of decontaminating substance; and a vaporizer positioned within the decontamination chamber in fluid communication with the source of decontaminating substance and the container and configured to vaporize the decontaminating substance.

Also disclosed herein is a method for decontaminating a device, comprising positioning a container containing a device to be decontaminated in a decontamination chamber, the device containing at least one lumen. The method includes connecting the container to a source of decontaminating substance located within the decontamination chamber; reducing the pressure in the decontamination chamber containing the container; vaporizing the decontaminating substance in the reduced pressure decontamination chamber; and injecting the vaporized decontaminating substance into the lumen of the device to be decontaminated.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The instant disclosure includes a system for decontamination of a device by directly injecting a vaporized decontaminating substance into the device while controlling the pressure and temperature of the system. In some embodiments, the system includes a decontamination chamber for enclosing a device to be decontaminated, a first source of decontaminating substance and a first vaporizer located within the decontamination chamber, and a second source of decontaminating substance and a second vaporizer outside the decontamination chamber. The system may be used to decontaminate a device through a decontamination process having one or more decontamination cycles.

Figure 1:
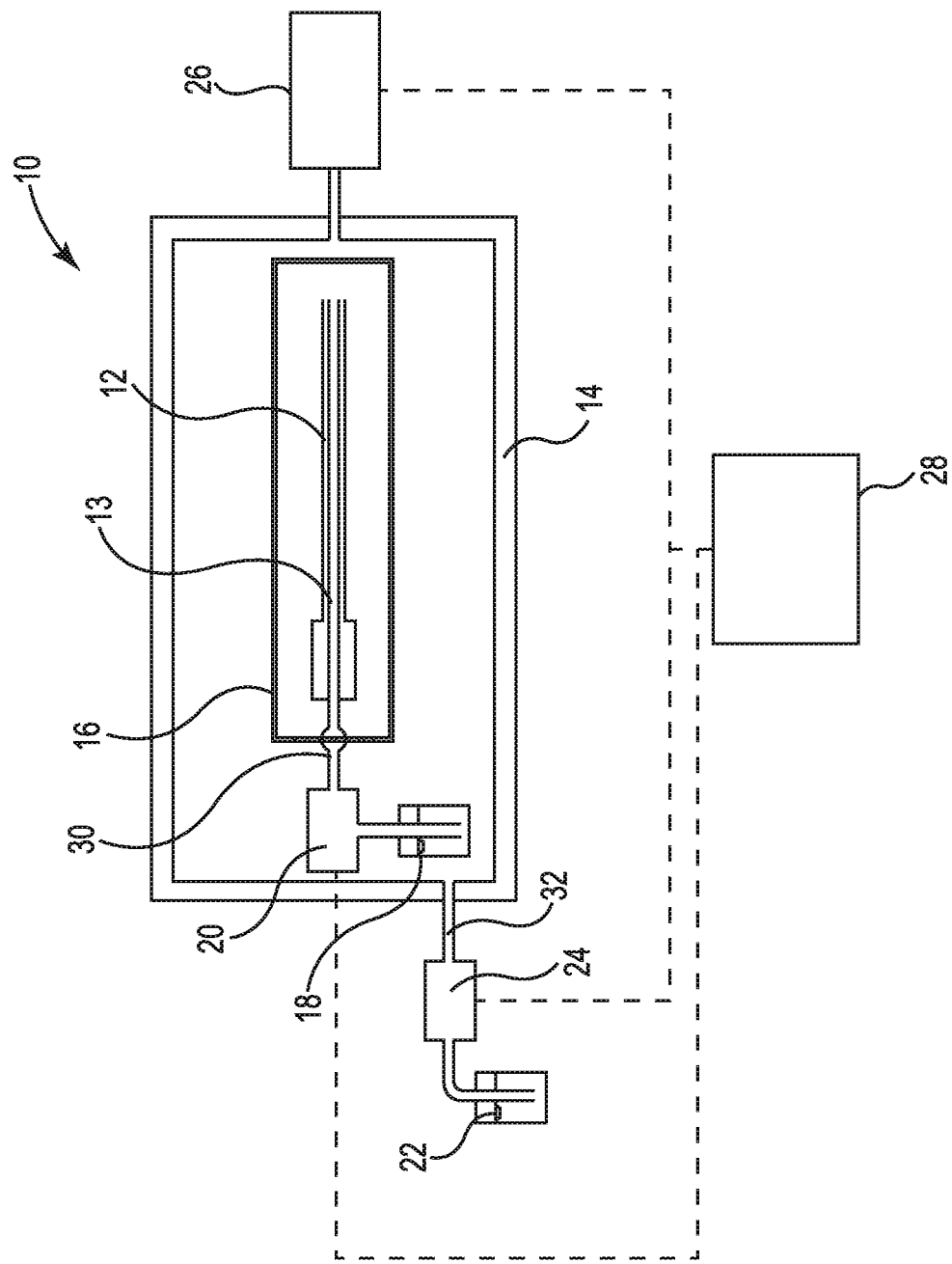
FIG. 1 is a schematic view of a decontamination system.

FIG. 1 is a schematic view of one embodiment of a system 10 for decontaminating a medical, dental, or other device 12 which may include one or more lumens 13 extending therethrough. System 10 may include a decontamination chamber 14, a container 16, a first source of decontaminating substance 18, first vaporizer 20, a second source of decontaminating substance 22, second vaporizer 24, an environmental monitoring and control system 26 which includes a vacuum pump, and a system control system 28. The container 16 containing the device 12 is positioned within the decontamination chamber 14.

In some embodiments, the first source of decontaminating substance 18 and first vaporizer 20 may be positioned within decontamination chamber 14. In some embodiments, the first source of decontaminating substance 18 may be connected or attached to container 16. For example, first source of decontaminating substance 18 and first vaporizer 20 may clip-to or otherwise directly attach to the container 16. In some embodiments, first source of decontaminating substance 18 and first vaporizer 20 may attach or connect to container 16 by conduit 30. For example, conduit 30 may pass through an opening formed in container 16 such that first source of decontaminating substance 18 flows directly into container 16 without, for example, passing through decontamination chamber 14. In some embodiments, first source of decontaminating substance 18 and first vaporizer 20 may be in direct fluid communication with one or more lumens 13 of device 12. For example, conduit 30 may direct decontaminating substance from first vaporizer 20 to one or more lumens 13 of device 12.

The first source of decontaminating substance 18 may include a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, Va.: AAMI 2005). In some embodiments, suitable decontamination substances include a room temperature (e.g., 20° C. to 25° C.) substance that can be dispersed as a fluid, such as a liquid, a vapor, or a combination thereof (such as a fog) during the decontamination process. For example, suitable decontamination substances include hydrogen peroxide ($H_2O_2$) and/or peracetic acid (PAA).

The first source of decontaminating substance 18 may be provided in a premeasured volume or in bulk volume. For example, the first source of decontaminating substance 18 may be provided as a premeasured volume in a suitable amount necessary for a single decontamination cycle or decontamination process. For example, where a decontamination process includes two cycles, two premeasured volumes may be provided for a complete decontamination process. In some embodiments, the first source of decontaminating substance 18 may be provided in an enclosed or sealed container or package, such as a pod. In some embodiments, the first source of decontaminating substance 18 may be released from the package by puncturing or otherwise forming an opening in at least a portion of the package. The package may be punctured at any suitable time during the decontamination process. For example, the package may be punctured upon positioning within decontamination chamber 14. In another example, the package may be punctured at a specified time during the decontamination process, for example, after vacuum conditions are established in decontamination chamber 14. In some embodiments, releasing the first source of decontaminating substance 18 from the package after decreasing the pressure in the decontamination chamber 14 may preserve the integrity of the chemistry of the first source of decontaminating substance 18. For example, in some embodiments, the package or container may protect the first source of decontaminating substance 18 from the conditions within the decontamination chamber 14 until shortly before the first source of decontaminating substance 18 is required. In some embodiments, the package or container may prevent loss of water and/or chemistry (i.e. hydrogen peroxide or peracetic acid) from the decontaminating substance 18, such as through vaporization, at low pressure.

Additionally or alternatively, the first source of decontaminating substance 18 may be provided as a bulk liquid and the volume of decontaminating substance 18 may be directed to the first vaporizer 20 as necessary. That is, the first source of decontaminating substance 18 may be provided in a volume greater than required for the decontamination cycle or process. In some embodiments, a valve or other closure device may be used to prevent or minimize exposure of the first source of decontaminating substance 18 to conditions within the decontamination chamber 14, such as vacuum conditions, until shortly before the use of the first source of decontaminating substance 18 in a decontamination cycle or process.

The first vaporizer 20 forms decontaminating substance 18 into a vapor, fog or other suitable form for the decontamination process. For example, first vaporizer 20 may heat decontaminating substance 18 in liquid form to vaporize or otherwise transform liquid decontaminating substance 18 into a vapor or fog. In some embodiments, decontaminating substance 18 may be pulled into the first vaporizer 20. In other embodiments, decontaminating substance 18 may be pushed into the first vaporizer 20.

The second source of decontaminating substance 22 and second vaporizer 24 may be positioned outside decontamination chamber 14 and may be in fluid communication with decontamination chamber 14. For example, in some embodiments, second source of decontaminating substance 22 and second vaporizer 24 may be connected to decontamination chamber 14 by channel 32. In some embodiments, the second source of decontaminating substance 22 and second vaporizer 24 direct decontaminating substance to decontamination chamber 14.

The second source of decontaminating substance 22 may include a chemical or other substance suitable for use in a decontamination process as described herein with respect to the first source of decontaminating substance 18. In some embodiments, the first source of decontaminating substance 18 and the second source of decontaminating substance 22 include the same decontamination substance. In other embodiments, the first source of decontaminating substance 18 and the second source of decontaminating substance 22 may include different decontamination substances. The second source of decontaminating substance 22 may be provided as a premeasured volume or as a bulk volume, as described herein with respect to the first source of decontaminating substance 18.

Second vaporizer 24 forms second source of decontaminating substance 22 into a vapor, fog or other suitable form for the decontamination process. In some embodiments, the second vaporizer 24 may be the same as or may be different than the first vaporizer 20.

The system control system 28 provides control signals to and/or receives condition sensing and equipment status signals from the decontamination chamber 14, environmental monitoring and control system 26, first source of decontaminating substance 18, first vaporizer 20, second source of decontaminating substance 22 and second vaporizer 24. For example, the system control system 28 controls delivery of the decontaminating substance from the first source of decontaminating substance 18 to the first vaporizer 20. Additionally or alternatively, the system control system 28 controls delivery of the decontaminating substance from the second source of decontaminating substance 22 to second vaporizer 24.

The environmental monitoring and control system 26 may adjust the environmental conditions within the decontamination chamber 14. For example, the environmental monitoring and control system 26 may provide control signals to and/or receives condition sensing and equipment status signals from a vacuum pump or other device for adjustment of the pressure of the decontamination chamber 14.

Container 16 forms an enclosed space and holds at least one device 12. In some embodiments, container 16 may have one or more soft or flexible sides or portions. For example, container 16 may be a pouch. In some embodiments, container 16 may have one or more hard or rigid sides. For example, container 16 may be a case or other enclosure. In some embodiments, container 16 may include a combination of rigid and flexible portions. For example, container 16 may have a rigid bottom and sides and may have a flexible top or lid.

Container 16 may have at least one portion, for example at least one side or top, through which the second source of decontaminating substance 22 may penetrate or permeate. For example, in some embodiments, the second source of decontaminating substance 22 may flow from the second vaporizer 24 through the channel 32 into the decontamination chamber 14 where it may decontaminate the outer surface of the container 16. The second source of decontaminating substance 22 in the decontamination chamber 14 may also permeate through at least one portion of the container 16 so as to enter container 16 and may decontaminate at least a portion of the outer surface of device 12. In some embodiments, the container 16 may be disposable. In other embodiments, the container 16 may be reusable.

Figure 2:
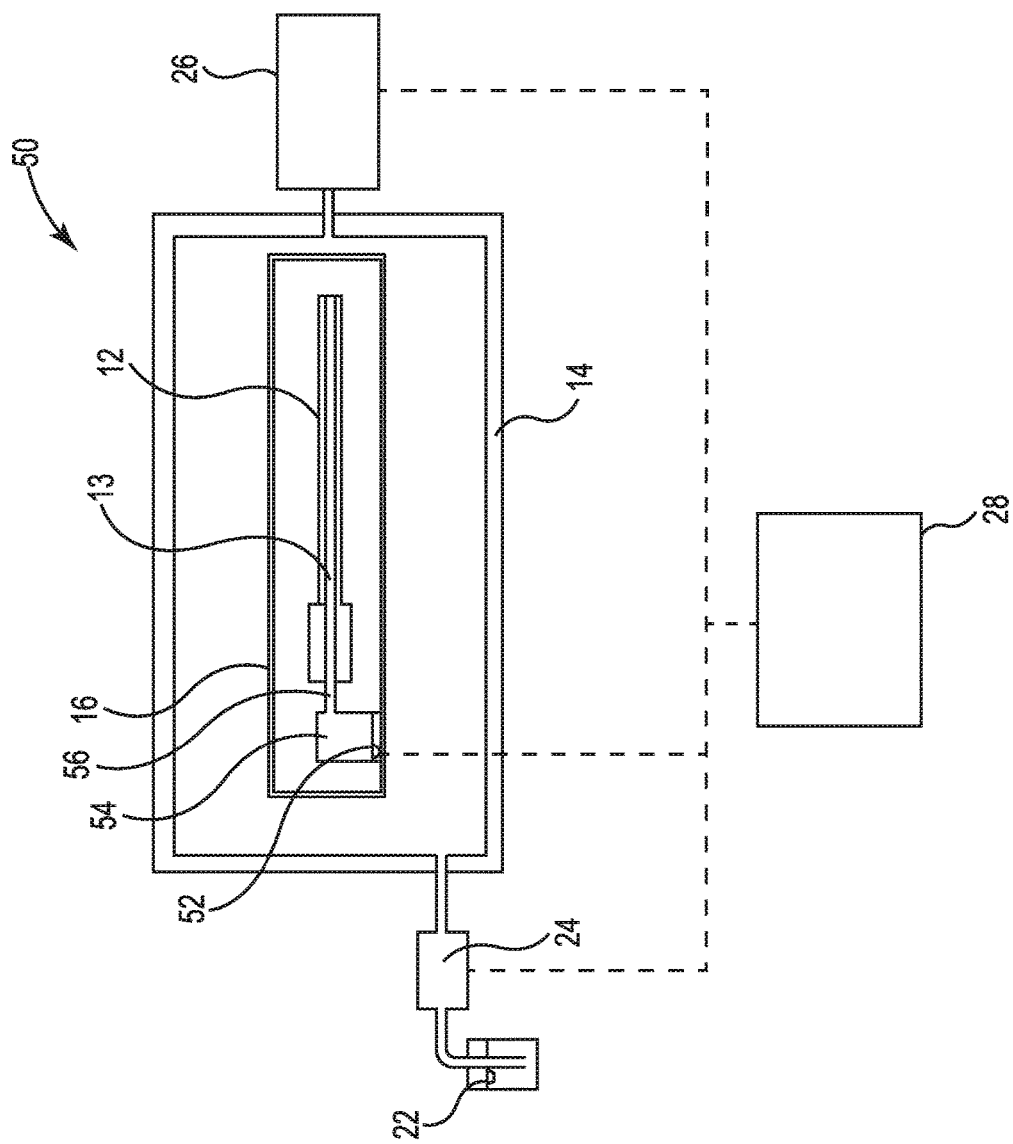
FIG. 2 is a schematic view of an alternative decontamination system.

FIG. 2 is a schematic view of an alternative embodiment of decontamination system 50. In some embodiments, the system 50 includes a decontamination chamber 14, a container 16, a first source of decontaminating substance 52 and a first vaporizer 54, a second source of decontaminating substance 22 and second vaporizer 24, an environmental monitoring and control system 26 and a system control system 28.

The first source of decontaminating substance 52 and first vaporizer 54 are located within the decontamination chamber 14. In some embodiments, the first source of decontaminating substance 52 and the first vaporizer 54 are both located within the container 16. First vaporizer 54 may be a heater capable of heating the first source of decontaminating substance 52 to a specified temperature, such as above the vapor temperature of the decontaminating substance. Suitable methods of heating may include electrical heating, such as resistance heating, inductive heating, microwave, infrared heating, and conductive heating.

In some embodiments, the first source of decontaminating substance 52 may be provided in a predetermined volume, such as a volume suitable for a decontamination process or a portion of a decontamination process, such as a single decontamination cycle. The first source of decontaminating substance 52 may be provided in a reusable or a disposable package. In some embodiments, the first source of decontaminating substance 52 may be provided as a predetermined volume in a sealed container which may be punctured or otherwise at least partially opened to enable the first source of decontaminating substance 52 to exit or leave the package during a decontamination process. For example, the first source of decontaminating substance 52 may be provided in a package which may be punctured once positioned within the container 16. In some embodiments, the package may be punctured after the package is positioned within the container 16 and the container 16 is sealed or otherwise closed. In other embodiments, the package may be punctured at a specified time during the decontamination process, for example, after vacuum conditions are established in the decontamination chamber 14. As discussed herein with respect to the first source of decontaminating substance 52, the package may protect the first source of decontaminating substance 52 from the conditions within the decontamination chamber 14 until shortly before the first source of decontaminating substance 52 is required for the decontamination cycle.

In some embodiments, the first source of decontaminating substance 52 may be provided in a package that is integral with the container 16. For example, the container 16 may be provided with a package containing a pre-determined amount of first source of decontaminating substance 52.

In other embodiments, the first source of decontaminating substance 52 may be provided in a package which is removable from the container 16. In some embodiments, the package may be positioned within the container 16 and may be punctured or otherwise at least partially opened shortly before or immediately before the first source of decontaminating substance 52 is required for the decontamination cycle.

In some embodiments, the first source of decontaminating substance 52 may be provided in a container which is placed within the first vaporizer 54 and the first source of decontaminating substance 52 may be released from the container when subjected to heat from the first vaporizer 54. For example, the container may be placed within a coil or block heater of the first vaporizer 54. In some embodiments, the first source of decontaminating substance 52 may be provided in a reusable container which may be loaded with a pre-determined amount of first source of decontaminating substance 52 prior to a decontamination process. For example, a pre-determined amount of first source of decontaminating substance 52 may be measured, such as by volume or mass, and added to the container. In some embodiments, a measuring device such as a syringe may be used to measure and transfer a pre-determined amount of the first decontaminating substance 52 to the container.

In some embodiments, the first source of decontaminating substance 52 may be connected to lumen 13 of device 12. For example, the first source of decontaminating substance 52 may be connected to lumen 13 by conduit 56. In some embodiments, the decontamination system 50 may include one or more valves to direct the first source of decontaminating substance 52 to one or more specified lumens.

Figure 3:
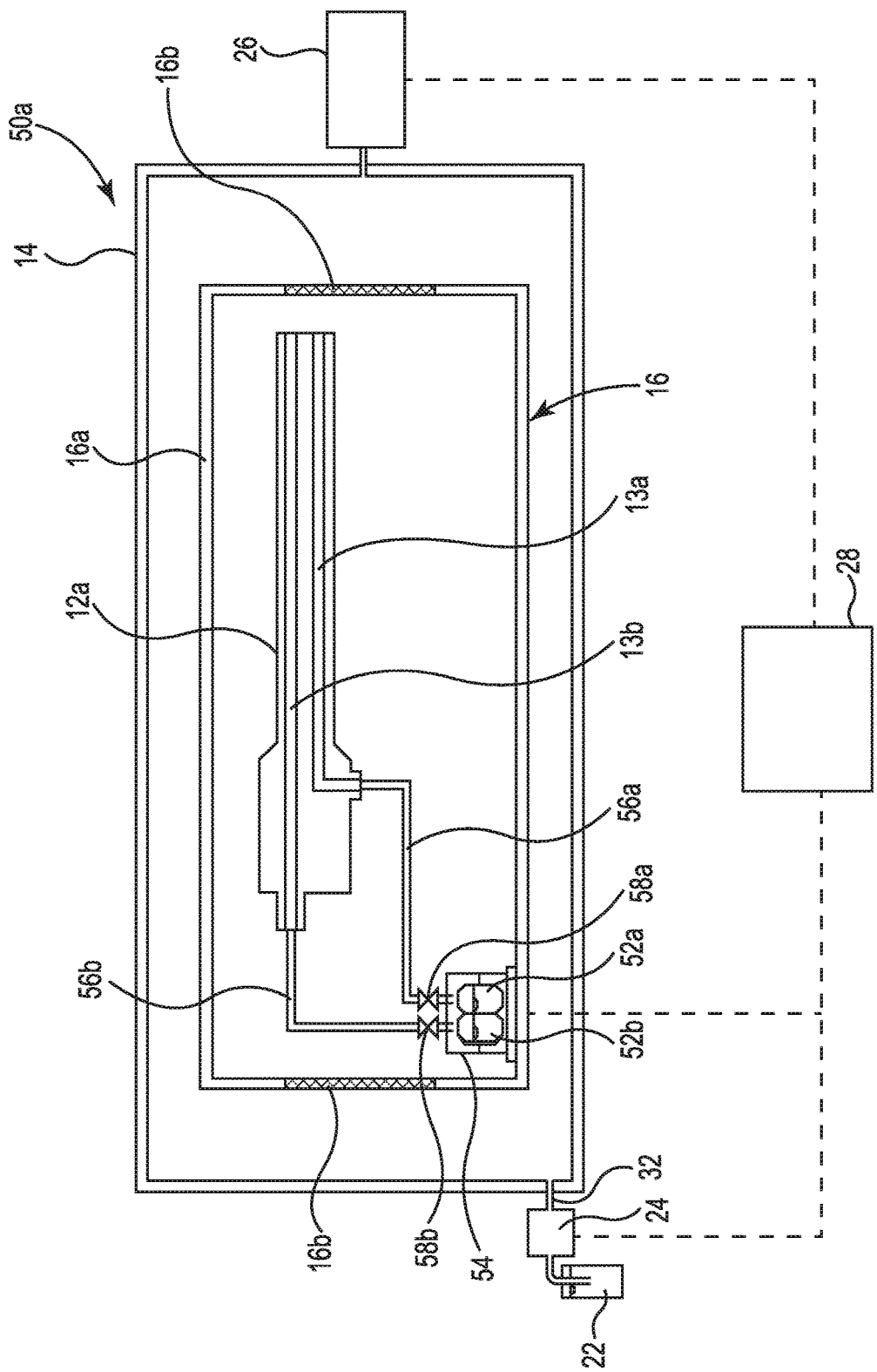
FIG. 3 is a schematic view of a decontamination system for a multilumen device.

FIG. 3 is a schematic view of an embodiment of a system 50a for decontamination of a multilumen device 12a. In some embodiments, system 50a includes decontamination chamber 14, container 16, first source of decontaminating substance 52a, 52b, first vaporizer 54, second source of decontaminating substance 22, second vaporizer 24, an environmental monitoring and control system 26 and a system control system 28. System 50a includes first vaporizer 54 connected to first lumen 13a and second lumen 13b by first conduit 56a and second conduit 56b, respectively. First sources of decontaminating substance 52a and 52b may be located within the decontamination chamber 14. First vaporizer 54 may be located within decontamination chamber 14 and in communication with two first sources of decontaminating substance 52a and 52b. Second source of decontaminating substance 22 and second vaporizer 24 may be located outside of decontamination chamber 14 and in fluid communication with decontamination chamber 14 via channel 32. During use, first sources of decontaminating substance 52a and 52b may be provided in a predetermined volume in a package, and second source of decontaminating substance 22 may be provided in a predetermined volume in a package. The packages of first sources of decontaminating substance 52a and 52b may be punctured or an opening may be formed therein to release the decontaminating substances into first vaporizer 54. In some embodiments, the packages of first sources of decontaminating substance 52a and 52b may be punctured or opened at the same time. In other embodiments, the packages of first sources of decontaminating substance 52a and 52b may be opened at different periods of time. For example, the package of first source of decontaminating substance 52a and 52b may be opened at a first time period during the decontamination process and the package of second source of decontaminating substance 22 may be opened at a later period of time during the decontamination process.

First valve 58a may regulate or control the flow from first vaporizer 54 to the first lumen 13a, and second valve 58b may regulate or control the flow of the decontaminating substance from first vaporizer 54 to the second lumen 13b. In some embodiments, system control system 28 may control valves 58a and 58b. First valve 58a and second valve 58b may include flow regulators to control flow rate through first conduit 56a and second conduit 56b. For example, it may be desirable to control the flow rates through first conduit 56a and second conduit 56b when the device has lumens of different diameters. For example, a flow rate through the first conduit 56a may be selected to be different than a flow rate through the second conduit 56b if the first lumen 13a has a different diameter or length than that of the second lumen 13b. For example, the first valve 58a may have a flow regulator suitable for providing vaporized decontaminating substance to a lumen having an inner diameter of 1 mm, while the second valve 58b may have a flow regulator suitable for providing vaporized decontaminating substance to a lumen having an inner diameter of 4 mm. Using such a system, a device containing multiple lumens which may have different diameters may be decontaminated.

In some embodiments, valves 58a and 58b may be controlled such that the decontaminating substance flows through a single lumen at a time. For example, first valve 58a may be closed when second valve 58b is open and the decontaminating substance from vaporizer 54 can flow through the second lumen 13b while it is prevented from flowing through the first lumen 13a. Although first vaporizer 54 is shown containing two first sources of decontaminating substance 52a and 52b, the first vaporizer 54 may contain any number of first sources.

System 50a may also include container 16 having a surface having rigid portions 16a and permeable portions 16b. In some embodiments, permeable portions 16b may be permeable by the decontaminating substance. For example, in some embodiments, decontaminating substance may flow from the first vaporizer 54 into decontamination chamber 14 and then permeate through permeable portions 16b of container 16 into the container 16.

The length of conduits 56a and 56b that carry the vapor from the first vaporizer 54 to the lumens 13a and 13b are selected to provide a suitable distance for the vapor to travel from the first vaporizer 54 to the lumen. In some embodiments, the temperature of a vapor exiting the first vaporizer 54 is about 75° C. to about 95° C. Certain devices, such as endoscopes, often cannot tolerate temperatures above 60° C. without sustaining damage. Using a system that vaporizes a decontaminating substance, and then allows the vapor to cool below 60° C. before contacting the device, allows decontamination of an endoscope without damaging it. In some embodiments, conduits 56b and 56a have a suitable length that allows the vapor to cool from the temperature of the vaporizer to below 60° C. before it contacts the device. For example, the conduits 56b and 56a that carry the vapor from the first vaporizer 54 to lumens 13a and 13b may be approximately 20 cm long.

Figure 4:
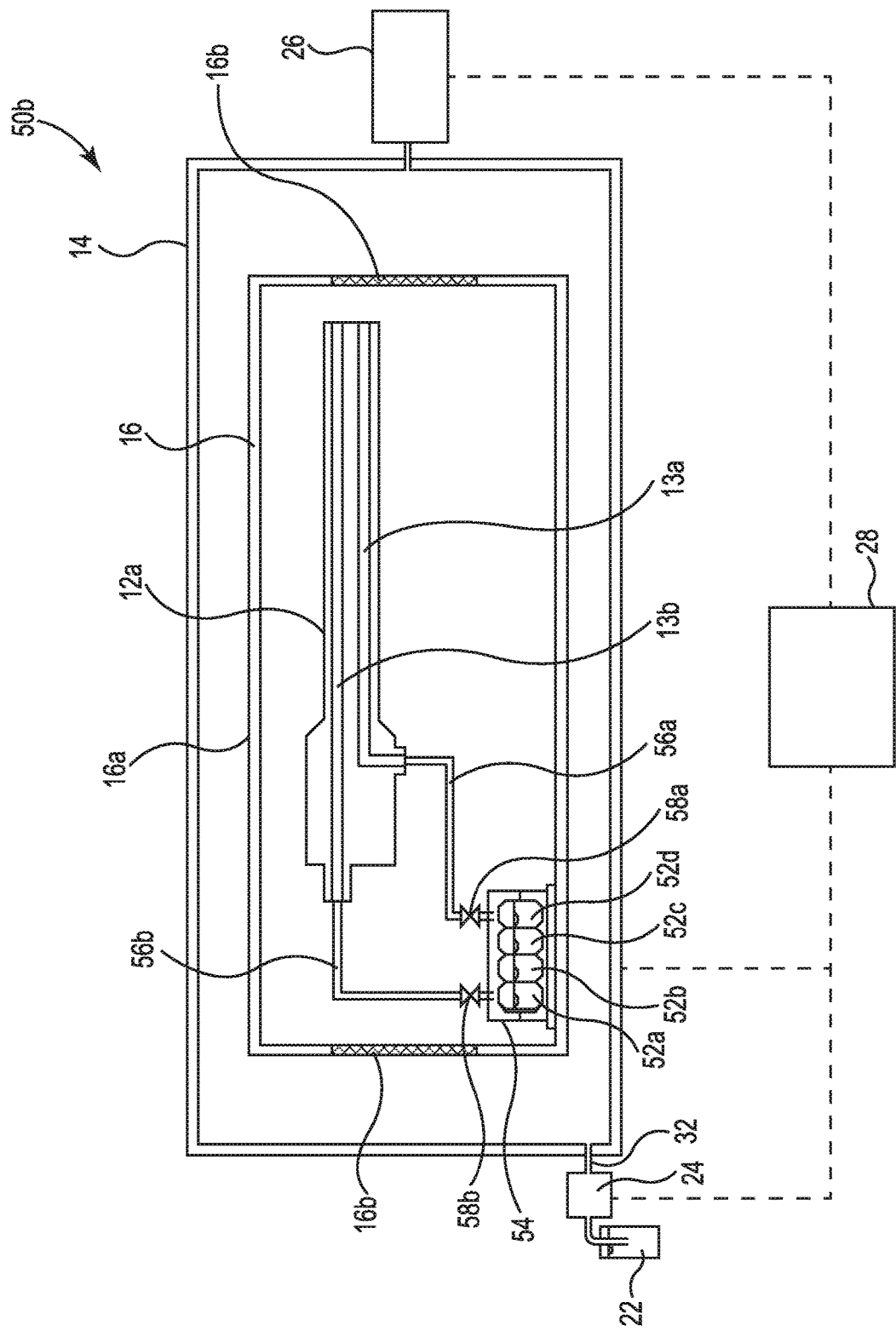
FIG. 4 is a schematic view of an alternative decontamination system for a multilumen device.

FIG. 4 is a schematic view of an embodiment of a system 50b for decontamination of a multilumen device 12a. System 50b includes decontamination chamber 14 and a first vaporizer 54 which is connected to four first sources of decontaminating substance, 52a, 52b, 52c and 52d. In some embodiments, system 50b also includes second source of decontaminating substance 22, second vaporizer 24, an environmental monitoring and control system 26 and a system control system 28.

In some embodiments, the first vaporizer 54 is located within the decontamination chamber 14 and connected to first lumen 13a and second lumen 13b of multilumen device 12a. During use, first sources of decontaminating substance, 52a, 52b, 52c and 52d may be provided in a predetermined volume, for example in a package. The decontaminating substance may be released from the packages of 52a, 52b, 52c and 52d at the same time or during different periods of time during a decontamination process. The packages of 52a, 52b, 52c and 52d may be punctured or an opening may be formed therein to release the decontaminating substance into first vaporizer 54. In some embodiments, the packages of first sources of decontaminating substance 52a, 52b, 52c and 52d may be punctured or opened at the same time. In other embodiments, the packages of first sources of decontaminating substance 52a, 52b, 52c and 52d may be opened at different periods of time. For example, the package of first sources of decontaminating substance 52a and 52b may be opened at a first time period during the decontamination process and the package of first sources of decontaminating substance 52c and 52d may be opened at a later period of time during the decontamination process.

When released, the decontaminating substance flows into the first vaporizer 54 where it may be vaporized. The decontaminating substance flows from the first vaporizer 54 to either the first lumen 13a or the second lumen 13b through first conduit 56a or second conduit 56b, respectively.

First valve 58a controls the flow to first conduit 56a and second valve 58b controls the flow to second conduit 56b as described herein. In some embodiments, first valve 58a and second valve 58b may be controlled by system control system 28. As described herein, the valves may be controlled so that the decontaminating substance flows through one lumen at a time. For example, first valve 58a may be closed when second valve 56b is open and the decontaminating substance from first vaporizer 54 can flow through the second lumen 13b while it is prevented from flowing through the first lumen 13a.

System 50b may also include container 16 having an outer surface having rigid portions 16a and permeable portions 16b. In some embodiments, permeable portions 16b may be permeable by the decontaminating substance. For example, in some embodiments, decontaminating substance may flow from second vaporizer 24 into decontamination chamber 14 and then permeate through permeable portions 16b of container 16 into the container 16.

Figure 5:
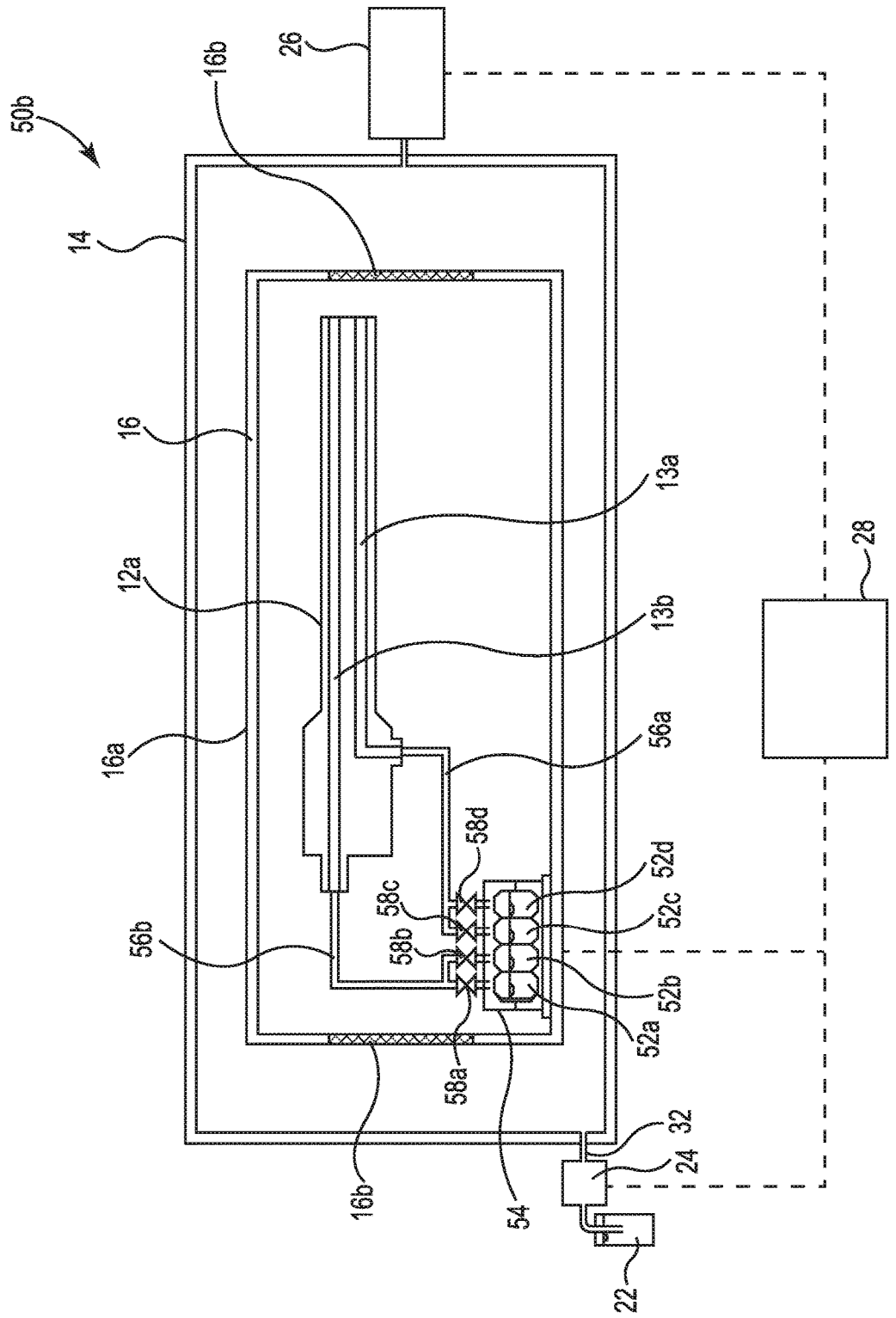
FIG. 5 is a schematic view of a further alternative decontamination system for a multilumen device.

FIG. 5 is a schematic view of an embodiment of a system 50c for decontamination of a multilumen device 12a. The system 50c includes a first vaporizer 54 which is located within the decontamination chamber 14 and is connected to four first sources of decontaminating substance, 52a, 52b, 52c and 52d. In some embodiments, the first vaporizer 54 is connected to first lumen 13a of multilumen device 12a via first conduit 56a, and second lumen 13b of multilumen device 12a via second conduit 56b. During use, first sources of decontaminating substance, 52a, 52b, 52c and 52d may be provided in a predetermined volume, for example in a package. In some embodiments, system 50c also includes second source of decontaminating substance 22, second vaporizer 24, an environmental monitoring and control system 26 and a system control system 28.

In system 50c the decontaminating substance is vaporized in the provided package and directed down a specified conduit. For example, first source of decontaminating substance 52a is vaporized in the provided package and then flows directly to second conduit 56b. That is, vaporized first source of decontaminating substance 52a does not flow into a common space within first vaporizer 54 where it may mix with first source of decontaminating substance 52b, 52c and/or 52d before flowing to second conduit 56b.

In some embodiments, first valve 58a controls the flow of vaporized decontaminating substance from first source of decontaminating substance 52a to second conduit 56b and second lumen 13b. Second valve 58b controls the flow of vaporized decontaminating substance from first source of decontaminating substance 52b to second conduit 56b and second lumen 13b. Third valve 58c controls the flow of vaporized decontaminating substance from first source of decontaminating substance 52c to first conduit 56a and first lumen 13a. Fourth valve 58d controls the flow of vaporized decontaminating substance from first source of decontaminating substance 52d to first conduit 56a and first lumen 13a. Valves 58a, 58b, 58c and 58d may be controlled by system control system 28. As described herein, system control system 28 may control the valves such that the decontaminating substance flows through one lumen at a time.

System 50c may be used with container 16 having an outer surface having rigid portions 16a and permeable portions 16b. In some embodiments, permeable portions 16b may be permeable by the decontaminating substance. For example, in some embodiments, decontaminating substance may flow from second vaporizer 24 into decontamination chamber 14 and then permeate through permeable portions 16b of container 16 into the container 16.

Thus, in an overall configuration, to decontaminate the device 12 shown in FIGS. 1, 2, and 3 or multilumen device 12a shown in FIGS. 4 and 5, the device 12 or multilumen device 12a may be placed within the container 16 and connected to the first source of decontaminating substance. For example, the device 12 or multilumen device 12a may be connected to the first source of decontaminating substance by a conduit 30, 56, or conduits 56a, 56b. The device 12 or multilumen device 12a may be sealed within the container 16 and placed in the decontamination chamber 14. The device 12 or multilumen device 12a is then subjected to a decontamination process which may include one or more decontamination cycles.

As described herein, a decontamination cycle includes at least one release of decontaminating substance into the decontamination chamber 14 for decontaminating the device 12 or multilumen device 12a. In some embodiments, a decontamination process may include two or more identical decontamination cycles. In some embodiments, the first step of a decontamination cycle may be decreasing the pressure within the decontamination chamber 14 below atmospheric pressure, and the last step may be returning the pressure within the decontamination chamber 14 to atmospheric pressure. In some embodiments, a decontamination process begins when a device 12 or multilumen device 12a is placed with the decontamination chamber 14, and ends when the device 12 or multilumen device 12a is removed from the decontamination chamber 14. After device 12 or multilumen device 12a is placed within decontamination chamber 12, the pressure within the chamber may be decreased to a suitable range, such as to a pressure less than about 10 Torr.

In some embodiments, a decontamination cycle includes transferring a predetermined amount of a decontaminating substance, such as aqueous hydrogen peroxide or peracetic acid, to a package such as a vial, which is then placed into the decontamination chamber 14, for example in a vial holder. A predetermined amount may be measured for example by volume or weight. In some embodiments, the decontaminating substance may contain about 59% hydrogen peroxide, and the balance water. Devices to be sterilized such as those containing a lumen or lumens are placed in a container attached to a conduit 30, 56, or conduits 56a, 56b. The container is positioned within the decontamination chamber. The conduit 30, 56, or conduits 56a, 56b. are also connected to a vaporizer. The chamber is then closed and locked. Vacuum is drawn in the decontamination chamber.

Decontaminating substance is introduced into the decontamination chamber 14. In some embodiments, a first decontaminating substance may be directly injected into the device 12 or multilumen device 12a. In some embodiments, a second decontaminating substance may be introduced into the decontamination chamber 14 and penetrate the container 16. In some embodiments, the decontaminating substance may be introduced when the pressure of the decontamination chamber 14 is lower than atmospheric pressure, for example less than about 10 Torr. As discussed herein, first decontaminating substance is introduced directly into the container 16. For example, the first decontaminating substance may be introduced directly into one or more lumens 13, 13a, 13b of the device 12 or multilumen device 12a. First decontaminating substance flows through and provides decontamination of the one or more lumens 13, 13a, 13b. In some embodiments, first decontaminating substance is provided in a premeasured volume sufficient to decontaminate the device 12 or multilumen device 12a, and in particular the lumens 13, 13a, or 13b during the decontamination process. The second decontaminating substance may be introduced into the decontamination chamber 14. For example, the second decontaminating substance may flow directly into the decontamination chamber 14 and may decontaminate the outer surface of container 16. The second decontaminating substance may also permeate at least a portion of container 16 such that the second decontaminating substance enters the container 16. In such an example, the second decontaminating substance may decontaminate the outer surface of the device 12 or multilumen device 12a. In some embodiments, first decontaminating substance and second decontaminating substance may be introduced simultaneously. In other embodiments, first and second decontaminating substances may be introduced separately.

In some embodiments, the decontaminating substance such as an aqueous solution of hydrogen peroxide or peracetic acid is injected into the vaporizer. In some embodiments, vapor is generated by delivering decontaminating substance into the second 24 vaporizer where the decontaminating substance is heated and vaporized. The vapor is then introduced into the decontamination chamber 14, under sub-ambient pressure where it will surround the items to be sterilized. This first step allows decontamination of the device's outer surface. The decontaminating substance may be allowed to surround the items to be sterilized such as the lumen or lumens. After a period of time to allow diffusion of the decontaminating substance, the pressure is reduced in the decontamination chamber 14, and both the vaporizer and the chamber are exposed to deep vacuum. In some embodiments, a second injection is then performed in the first vaporizer 20, 54. During the second injection, a decontaminating substance is directly injected into the lumen or lumens in a step manner to reduce the injection speed and allow the decontaminating substance to vaporize and avoid any re-condensation.

The decontaminating substance may be held in decontamination chamber 14, container 16 and/or device 12 or multilumen device 12a for a period of time to facilitate the decontamination of the container 16 and the device 12 or multilumen device 12a, including lumens 13, 13a, 13b. When the decontaminating substance has been held for the desired or programmed amount of time, the system control system 28 can vent the decontamination chamber 14 to a higher, but in some embodiments, sub-atmospheric pressure. The system control system 28 can then hold the pressure within the decontamination chamber 14 for a period of time to further facilitate the decontamination of the device. After the decontaminating substance level reaches a plateau, an air wash is used to remove the vapor from the decontamination chamber 14 and device to be sterilized, such as the lumen or lumens. During the air wash, the system control system 28 increases the pressure within the decontamination chamber 14 and then decreases the pressure within the decontamination chamber 14. The system control system 28 may repeat these steps of increasing and decreasing the pressure within the decontamination chamber 14 multiple times to carry out an air wash of the decontamination chamber 14 and or device 12 or multilumen device 12a. After the air wash, the vacuum may be released and the chamber and vaporizer returned to atmospheric pressure by venting through a high efficiency particulate air (HEPA) filter. The system control system 28 may evacuate the decontamination chamber 14 to remove the decontaminating substance residuals from the decontamination chamber 14. This decontamination cycle or series of steps may be repeated or extended as part of a comprehensive decontamination process.

Figure 6:
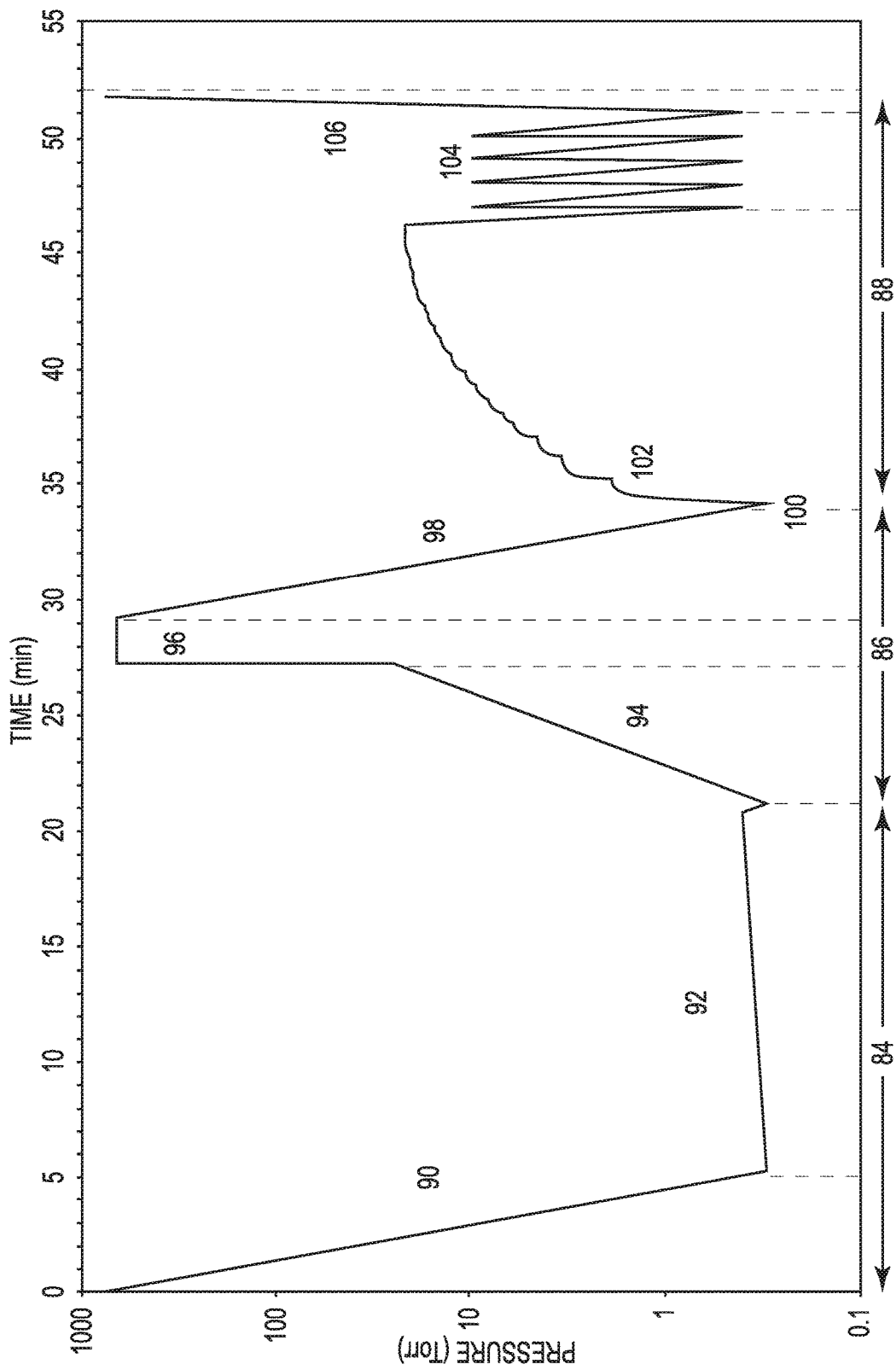
FIG. 6 is a graph showing pressure versus time in an exemplary decontamination cycle.

FIG. 6 shows a graph of pressure versus time within a decontamination chamber in an embodiment of a decontamination cycle. As shown in FIG. 6, in some embodiments, a decontamination cycle may include multiple pressure changes within a decontamination chamber. The decontamination cycle illustrated in FIG. 6 may be repeated several times within a decontamination process. The decontamination cycle may include certain steps such as a vacuum preconditioning 84, a first decontamination step 86, and a second decontamination step 88. The vacuum preconditioning 84 includes a pump down 90 in which pressure is drawn from the decontamination chamber and a lumen warm up period 92. During the lumen warm up period 92, the pressure within the decontamination chamber is held relatively steady.

In some embodiments, the vacuum preconditioning 84 may be followed by the first decontamination step 86. During the first decontamination step 86, decontaminating substance is injected into the decontamination chamber in a chamber injection step 94. During the chamber injection step 94 the pressure within the decontamination chamber increases. In an example embodiment, up to 2 mL of decontaminating substance is injected into the decontamination chamber during the chamber injection step 94. After the decontaminating substance in injected, it may be allowed to diffuse throughout the decontamination chamber in a diffusion period 96 while the pressure is held steady. After the diffusion period 96, a second pump down 98 may be carried out. During the second pump down 98, the pressure within the decontamination chamber decreases. In some embodiments, after the second pump down 98, the process includes a vaporizer pump down 100 in which a vacuum is pulled within the vaporizer.

In some embodiments, the second decontamination step 88 is carried out after the vaporizer pump down 100. During the second decontamination step 88, a device injection step 102 includes injecting decontaminating substance directly into the device within the decontamination chamber. For example, decontaminating substance may be directly injected into a lumen of the device. In some embodiments, from about 1 mL to about 3 mL, from about 1.7 mL to about 2.3 mL, or from about 1.9 mL to about 2.1 mL of decontaminating fluid may be directly injected into the lumens during the device injection step. In an example embodiment, up to 2 mL of decontaminating substance is injected into the lumens contained within the decontamination chamber during the device injection step 102. During or after the device injection step 102, the pressure within the decontamination chamber increases. After the device injection step 102, a plurality of air washes 104 may be carried out. As shown in FIG. 6, the plurality of air washes 104 may include increasing and decreasing the pressure within the decontamination chamber repeatedly. This may be carried any number of times to remove a suitable amount of decontaminating substance from the decontamination chamber. After a suitable number of air washes, the pressure within the decontamination chamber may be allowed to reach atmospheric pressure in a final vent step 106. A summary of the steps outlined above and an example duration and pressure at each step is included below in Table 1.

TABLE 1

Example time and pressure within decontamination chamber for a single cycle

| Stage | Duration (seconds) | Pressure (Torr) |
|---|---|---|
| Pump Down and Lumen Warm Up | 1320 | 0.3 |
| Chamber Injection | 360 | 25.2 |
| Diffusion | 120 | 660 |
| Pump Down | 240 | 0.4 |
| Device Injection | 720 | 24.4 |
| Vent (multiple repetitions) | 2 | 10 |
| Pump Down (multiple repetitions) | 60 | 0.4 |
| Final Vent | 25 | 10 |

Decontaminating processes consume time and equipment. Thus, it is desirable to reduce the time required for a decontamination process while still achieving the desired decontamination level. Decreasing the time required for effective decontamination of a device allows a user to decontaminate a larger number of devices in less time. In some embodiments, the device injection step described above, allows a user to directly introduce decontaminating substance into a device that has an elongated and/or tortuous flow path. For example, endoscopes or other devices that have lumens with a high length to width ratio may benefit from having the decontaminating substance directly injected into the interior of the lumen. By directly injecting decontaminating substance into the interior of a lumen, a more effective means for the decontaminating substance to contact the interior surface of the lumen is provided. This process also ensures that the entire interior surface of the lumen comes in contact with decontaminating substance. That is, direct injection increases the ability for the decontamination substance to penetrate the entire length of the lumen. One potential benefit of directly injecting decontaminating substance into a lumen is the decreased cycle time required for adequate decontamination along the entire length of the lumen.

In some embodiments, the rate at which the decontaminating substance is injected into a lumen affects the vaporization rate of the decontaminating substance within the lumen. It has been found that decreasing the volumetric injection rate of decontaminating substance increases its vaporization rate. Having an increased vaporization rate may lead to a more effective vaporization, which in turn allows for lower operating temperatures required for the vaporizer.

In some embodiments, directly injecting vaporized decontaminating substance into a lumen allows the decontamination chamber to operate at lower temperatures throughout a decontamination process while still ensuring sufficient decontamination of a device such as a lumen. A lower operating temperature is beneficial when decontaminating certain devices that may be sensitive to elevated temperatures. For example, endoscopes often cannot tolerate temperatures above 60° C. without sustaining damage. Using a process that first vaporizes the decontaminating substance, and allows the vapor to cool below 60° C. before contacting the lumen allows decontamination of an endoscope without damaging it. This may be achieved by providing a suitable travel distance that the vapor is carried through the conduit from where the vapor exits the vaporizer to the location where the vapor first contacts the lumen. The length of the conduit that carries the vapor between the vaporizer and the lumen allows the vapor to cool as it travels from the vaporizer to the lumen. For example, the conduit that carries the vapor from the vaporizer to the lumen may be approximately 20 cm long. This distance has been found to allow the vapor temperature to decrease below 60° C. by the time the vapor contacts the lumen.

In some embodiments, the decontaminating substance may cause corrosion on certain devices if left in contact with the device for prolonged periods of time, or if highly concentrated decontaminating substances are used. Corrosion may also occur if the decontaminating substance vapor condenses on the surfaces of the device. To reduce decontaminating substance condensation within a lumen, the temperature of the decontaminating chamber and the vapor within the lumen may be specifically tailored.

Suitable operating parameters have been identified for effectively and efficiently decontaminating a lumen that avoid pressures, temperatures, and exposure times that may lead to thermal degradation or corrosion of the lumen. Using the above operating parameters, it has been found that the decontamination process disclosed herein can effectively sterilize lumens 3.0 or 3.5 meters in length. The process disclosed herein has been found to successfully sterilize a lumen 3.5 meters in length, while maintaining the operating parameters of the decontamination cycle within the pressure and temperature tolerances of the lumen. The process disclose herein has been found to successfully sterilize lumens with inner diameters of 1 mm, 1.6 mm, 2 mm, and 3.45 mm and an outer diameter of 3 mm, 3.18 mm, 4 mm, and 4.76 mm. It has also been found that 2 mL of decontaminating substance containing 59% hydrogen peroxide is successful in decontaminating multiple lumens simultaneously without damaging the lumens, such as by corrosion or excess pressure.

It has been found that operating the vaporizer at about 95° C. and maintaining the decontamination chamber temperature at 58° C. minimizes condensation within the lumen. In an example, a decontamination chamber was set to operate at 58° C. throughout the decontamination process and the vapor temperature as it exits the vaporizer was set at 95° C. The lumen was attached to a header that connected the lumen to the vaporizer by a 20 cm separation. After traveling through the header, the vapor entering the lumen was found to be 55° C. which is within the acceptable operating temperature for the lumen. In some embodiments, condensation can also be minimized by flowing air through the lumen during a decontamination process.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A system for decontamination of a medical device, the system comprising:
    a decontamination chamber configured to withstand pressure changes;
    a vacuum pump configured to adjust the pressure within the decontamination chamber;
    a source of decontaminating substance containing hydrogen peroxide or peracetic acid and positioned within the decontamination chamber, the source of the decontaminating substance configured to be isolated from the decontamination chamber at a reduced pressure prior to vaporization;
    a container configured to be received within the decontamination chamber, the container forming an enclosed space and configured to enclose a medical device and provide fluid communication between the medical device and the source of decontaminating substance; and
    a vaporizer positioned within the decontamination chamber in fluid communication with the source of decontaminating substance and the container and configured to vaporize the decontaminating substance.

2. The system of claim 1, wherein the container has an outer surface and wherein at least a portion of the outer surface is permeable by vaporized decontaminating substance.

3. The system of claim 1, wherein the medical device contains a lumen and wherein the source of decontaminating substance is fluidly connected to one lumen of the medical device.

4. The system of claim 1, wherein the medical device contains at least two lumens and the system further comprises a valve connected to the source of decontaminating sub stance.

5. The system of claim 1, further comprising a second source of decontaminating substance positioned outside the decontamination chamber and in fluid communication with the decontamination chamber.

6. The system of claim 1, wherein the vaporizer is positioned at least partially within the container.

7. The system of claim 1, wherein the decontaminating substance is a liquid prior to vaporization.

8. The system of claim 1, wherein the vaporizer includes a heat source selected from the group consisting of a resistance heater, inductive heater, infrared heater, microwave heater, and conductive heater.

9. A method for decontaminating a device, the method comprising:
    positioning a container containing a device to be decontaminated in a decontamination chamber, the device containing at least one lumen;
    connecting the container to a source of decontaminating substance located within the decontamination chamber;

reducing the pressure in the decontamination chamber containing the container;

vaporizing, by a vaporizer positioned within the reduced pressure decontamination chamber, the decontaminating substance in the reduced pressure decontamination chamber, the decontaminating substance being isolated from the reduced pressure decontamination chamber prior to being vaporized; and injecting the vaporized decontaminating substance into the lumen of the device to be decontaminated.

10. The method of claim 9, wherein the decontaminating substance includes hydrogen peroxide or peracetic acid.

11. The method of claim 9, wherein vaporizing the decontaminating substance includes vaporizing at least 2.0 ml of a fluid containing about 59% hydrogen peroxide.

12. The method of claim 9, wherein the vaporized decontaminating substance is less than 60 degrees Celsius when injected into the lumen.

13. The method of claim 9, wherein the device includes a plurality of lumens and further comprising controllably directing the decontaminating substance through one or more select lumens of the device.

14. The method of claim 9, further comprising connecting a second source of decontaminating substance to the decontamination chamber, the second source of decontaminating substance positioned outside the decontamination chamber.

15. The method of claim 9, wherein the device contains at least two lumens having different inner diameters and further comprising using flow regulators to provide vaporized decontaminating substance to each lumen individually.

16. The method of claim 9, wherein the decontaminating substance is in liquid phase before the vaporizing step.

17. The method of claim 9, wherein the pressure in the decontamination chamber is less than 20 Torr before vaporizing the decontaminating substance.

18. The method of claim 9, wherein a predetermined volume of decontaminating substance is placed within the decontamination chamber and connected to the vaporizer before vaporizing the decontaminating substance.

19. The method of claim 9, further comprising flowing vaporized decontaminating substance having a first temperature through a conduit having a length configured to decrease the vaporized decontaminating substance to a second temperature below 60 degrees Celsius before injecting the vaporized decontaminating substance into the lumen of the device to be decontaminated.

20. The method of claim 9, further comprising repeating the steps of reducing the pressure in the decontamination chamber containing the container; vaporizing the decontaminating substance in the reduced pressure decontamination chamber; and injecting the vaporized decontaminating substance into the lumen of the device to be decontaminated.

* * * * *